(12) United States Patent
Gutman

(10) Patent No.: US 11,819,455 B1
(45) Date of Patent: Nov. 21, 2023

(54) INTRAOCULAR PRESSURE CONTROL DEVICE AND METHOD FOR VITREORETINAL SURGERY

(71) Applicant: Justin Gutman, Montclair, NJ (US)

(72) Inventor: Justin Gutman, Montclair, NJ (US)

(*) Notice: Subject to any disclaimer, the term of this patent is extended or adjusted under 35 U.S.C. 154(b) by 274 days.

(21) Appl. No.: 17/097,219

(22) Filed: Nov. 13, 2020

Related U.S. Application Data

(60) Provisional application No. 63/034,249, filed on Jun. 3, 2020.

(51) Int. Cl.
*A61F 9/007* (2006.01)
*A61M 5/158* (2006.01)
*A61M 5/168* (2006.01)
*A61M 39/22* (2006.01)

(52) U.S. Cl.
CPC ............. *A61F 9/007* (2013.01); *A61M 5/158* (2013.01); *A61M 5/168* (2013.01); *A61M 39/22* (2013.01); *A61M 2039/229* (2013.01)

(58) Field of Classification Search
CPC .. A61F 9/007; A61F 9/00781; A61F 9/00736; A61F 2009/0087; A61F 2009/00887; A61F 9/0008; A61F 9/00745; A61M 5/158; A61M 5/168; A61M 39/22; A61M 2039/229; A61M 2210/0612; A61M 1/84; A61M 1/77; A61M 1/74; A61M 5/142; A61M 1/0058; A61M 2205/3331; A61M 2205/3344; A61M 3/0229; A61M 39/00; A61M 5/1408; A61M 5/1424; A61M 5/16881; A61M 2005/1787; A61M 5/31593; A61M 5/3298; A61M 1/774; A61M 1/85; A61M 39/223; A61K 9/0048; A61B 2217/005; A61B 2217/007; A61B 2017/320084; A61B 1/313
See application file for complete search history.

(56) References Cited

U.S. PATENT DOCUMENTS

| | | | | |
|---|---|---|---|---|
| 4,909,783 A | * | 3/1990 | Morrison | A61F 9/00781 604/246 |
| 5,755,684 A | * | 5/1998 | Chen | A61M 1/77 604/35 |

(Continued)

*Primary Examiner* — Nicholas J. Weiss
*Assistant Examiner* — Brandon W. Levy
(74) *Attorney, Agent, or Firm* — John Rizvi; John Rizvi, P.A.—The Patent Professor®

(57) ABSTRACT

There is disclosed an auxiliary pressure maintainer for maintaining intraocular pressure during eye surgery. The pressure maintainer includes a hollow infusion tube terminating in a small diameter infusion needle. A connector is provided on the infusion tube to connect the infusion tube to a source of pressurized fluid. The pressure maintainer further includes a stabilizing base adjacent the infusion needle for stabilizing the needle against the surface of the eye and a flexible wire located in or on the infusion tube and adjacent the infusion needle for maintaining a bent shape of the infusion tube. An enlarged grip is attached to the infusion tube to assist in manipulating the infusion needle through an eye wall. A stopcock may be connected to the connector to control the flow of fluid pressure through the infusion needle. There is also disclosed a method of using the auxiliary pressure maintainer with a primary pressure infusion device during an eye surgery procedure.

19 Claims, 8 Drawing Sheets

(56) References Cited

U.S. PATENT DOCUMENTS

| | | | | |
|---|---|---|---|---|
| 5,766,211 A * | 6/1998 | Wood | ................ | A61M 1/63 604/32 |
| 2006/0084961 A1 * | 4/2006 | Kadziauskas | ........... | A61F 9/008 606/4 |
| 2009/0192458 A1 * | 7/2009 | Wang | ................ | A61F 9/0017 604/117 |
| 2014/0107625 A1 * | 4/2014 | Hanlon | ............. | A61B 17/3421 604/533 |
| 2017/0165114 A1 * | 6/2017 | Hallen | ............... | A61F 9/00736 |

* cited by examiner

INTRAOCULAR PRESSURE CONTROL DEVICE AND METHOD FOR VITREORETINAL SURGERY

CROSS-REFERENCE TO RELATED APPLICATION

This application claims the benefit of U.S. Provisional Patent Application No. 63/034,249, filed on Jun. 3, 2020, which is incorporated herein by reference in its entirety.

FIELD OF THE INVENTION

The present invention relates generally to eye or vitreoretinal surgery and surgical procedures, and more particularly, to a surgical device and method for maintaining adequate posterior eye chamber pressure during these procedures.

BACKGROUND OF THE INVENTION

Vision issues affect thousands of individuals and may result in the need for corrective surgery. For example, issues such as macular degeneration or holes, detached retinas, cataracts and the like may severely impair an individual's vision. Vitreoretinal surgery is a procedure in which such issues can wholly or partially be corrected. Vitreoretinal surgery or vitrectomy includes a group of procedures performed inside the eye with various surgical devices and instruments.

Maintaining fluid pressure in the eye is important before, during and after eye surgery to prevent complications such as eye bleeding. Vitreoretinal surgery is made possible and safe because the intraocular pressure is maintained throughout the surgery by an infusion system that pumps fluid into the eye via an infusion cannula, and thereby maintains the fluid pressure within the eye at an appropriate level during the course of the surgery. However, at times during the surgery, surgeons may encounter bleeding, which can be controlled using various maneuvers. An important one of these maneuvers is to increase the fluid pressure within the eye to achieve hemostasis or increase in the intraocular pressure to reduce or effectively stop the bleeding.

At the end of the surgery, the infusion cannula is removed leaving a wound that is often self-sealing. However, in cases where the wound resulting from the removal of the infusion cannula does not self-seal, air and liquid leak out from the wound causing the eye to lose pressure (become hypotonus). When this occurs, the surgeon must suture the wound and then perform a subsequent injection of air or liquid to re-inflate the eye. During these precious moments, in which the eye has become soft, bleeding may occur until the adequate eye pressure is re-established. Furthermore, suturing an eye that has lost its pressure is a far less controlled maneuver, and can be dangerous, risking injury to the delicate tissues of the eye if the suturing needle is not passed precisely.

Every year, hundreds of thousands of vitrectomies are performed in the United States to repair the various problems that occur in the posterior segments of the eye, and that number continues to rise. As described hereinabove, an infusion cannula is both inserted into and removed from the eye in every vitrectomy. A significant percentage of cases face the complications of post-operative hypotony and post-operative intraocular hemorrhage or bleeding due to wound leaks after the infusion cannula has been removed. Thus, cases involving such post-operative complications may run in the thousands or tens of thousands per year.

Accordingly, there is need for a solution to at least one of the aforementioned problems. For instance, there is an established need for a surgical infusion device which helps or prevents the risk of post-operative hypotony and/or post-operative intraocular hemorrhage due to wound leaks after the infusion cannula has been removed. There is further an established need for a surgical method or procedure to perform the vitrectomies in a manner that reduces or eliminates the above-described post-operative complications that may occur after a vitrectomy.

SUMMARY OF THE INVENTION

The present invention is directed to an auxiliary pressure maintainer for maintaining intraocular pressure during eye surgery. The pressure maintainer is configured be hands-free once placed into the eye. The pressure maintainer includes a hollow infusion tube terminating in a small diameter infusion needle. A connector is provided on the infusion tube to connect the infusion tube to a source of fluid pressure. The pressure maintainer further includes a stabilizing base adjacent the infusion needle for stabilizing the needle against the surface of the eye and a flexible wire located in or on the infusion tube and adjacent the infusion needle for maintaining a bent shape of the infusion tube. An enlarged grip is attached to the infusion tube to assist in manipulating the infusion needle through an eye wall. A stopcock or other externally operable valve may be connected to the connector to control the flow of fluid pressure through the infusion needle. There is also disclosed a method of using the auxiliary pressure maintainer with a primary pressure infusion device during an eye surgery procedure.

In a first implementation of the invention, a pressure control device for maintaining fluid pressure within an intraocular cavity during eye surgery comprises a pressure maintainer. The pressure maintainer includes a plastically flexible, pressure control infusion tube having a distal end and a proximal end. A stabilizing base is provided at the distal end of the pressure control infusion tube and extending radially outward of the pressure control infusion tube, A pressure control infusion needle extends distally from the stabilizing base and the distal end of the pressure control infusion tube. The pressure control infusion needle is in fluid communication with the pressure control infusion tube. The pressure maintainer further includes a grip carried by the pressure control infusion tube distally to the stabilizing base, and at or near the stabilizing base. The grip has a width larger than a diameter of the pressure control infusion tube.

In a second aspect, the pressure control device may further include a connector attached to the proximal end of the pressure control infusion tube. The connector may be configured to provide a disconnectable connection between the proximal end of the pressure control infusion tube and a source of pressurized fluid (liquid or air).

In another aspect, the connector may be a luer-lock connector.

In another aspect, the pressure control infusion tube may include a distal infusion tube and a proximal infusion tube connected to one another by a disconnectable connection connecting a distal end of the proximal infusion tube to a proximal end of the distal infusion tube. A proximal end of the proximal infusion tube may provide the proximal end of the pressure control infusion tube, and a distal end of the distal infusion tube may provide the distal end of the pressure control infusion tube. The pressure control infusion needle and the stabilizing base may be located at the distal infusion tube. In some embodiments, the disconnectable connection may be a luer-lock connection.

In another aspect, the pressure control infusion needle may be attached to the distal end of the pressure control infusion tube by a disconnectable connection. In some embodiments, the disconnectable connection may be a luer-lock connection.

In yet another aspect, the pressure control infusion needle may have a gauge from 27 to 32.

In another aspect, a distal surface of the stabilizing base facing the pressure control infusion needle may be flat.

In another aspect, the stabilizing base may include a central opening from which the pressure control infusion needle extends outwardly and distally.

In another aspect, the pressure control device may further include a valve and a main infusion tube. The valve may be configured to connect to a source of pressurized fluid. The proximal end of the pressure control infusion tube may be connectable to the valve. In turn, the main infusion tube includes a proximal end and a distal end, wherein the proximal end of the main infusion tube may be connectable to the valve, and the distal end of the main infusion tube may carry a main infusion needle having a greater gauge than the pressure control infusion needle. The valve may be operable to switch between a first position and a second position. In the first position, the valve may provide fluid communication from the source of pressurized fluid to the main infusion tube and may prevent fluid communication from the source of pressurized fluid to the pressure control infusion tube. In the second position, the valve may prevent fluid communication from the source of pressurized fluid to the main infusion tube and may provide fluid communication from the source of pressurized fluid to the pressure control infusion tube.

In yet another aspect, the valve may be further operable to switch to a third position, in which the valve may prevent fluid communication from the source of pressurized fluid to the main infusion tube and to the pressure control infusion tube.

In another aspect, the main infusion tube may be connectable to the valve by a disconnectable connection. In some embodiments, the disconnectable connection may be a luer-lock connection.

In another implementation of the invention, a method of performing an eye surgery procedure while maintaining fluid pressure within an intraocular cavity may comprise the steps of:
  providing a pressure control device comprising
    a valve,
    a pressure maintainer, comprising:
      a plastically flexible, pressure control infusion tube having a distal end and a proximal end, the proximal end connected to the valve,
      a stabilizing base provided at the distal end of the pressure control infusion tube and extending radially outward of the pressure control infusion tube.
      a pressure control infusion needle extending distally from the stabilizing base and the distal end of the pressure control infusion tube, wherein the pressure control infusion needle is in fluid communication with the pressure control infusion tube, and
      a grip carried by the pressure control infusion tube distally to the stabilizing base, and at or near the stabilizing base, the grip having a width larger than a diameter of the pressure control infusion tube, and
    a main infusion tube, comprising a proximal end and a distal end, wherein the proximal end of the main infusion tube is connected to the valve, and wherein the distal end of the main infusion tube carries a main infusion needle having a greater gauge than the pressure control infusion needle;
  connecting the valve to a source of pressurized fluid;
  inserting the main infusion needle through an eye wall and into an intraocular cavity of an eye through a first incision in the eye wall;
  operating said valve to direct a flow of pressurized fluid from the source of pressurized fluid through the main infusion tube and main infusion needle and into the intraocular cavity;
  inserting one or more surgical instruments into the intraocular cavity through one or more additional incisions in the eye wall;
  performing a surgical procedure with the one or more surgical instruments;
  forming a further incision through the eye wall by inserting the pressure control infusion needle through the eye wall, the further incision being smaller than the first incision;
  operating the valve to direct the flow of pressurized fluid through the pressure control infusion tube and pressure control infusion needle and into the intraocular cavity; and
  removing the main infusion needle from the first incision while feeding pressurized fluid into the intraocular cavity through the pressure control infusion tube and pressure control infusion needle.

In another aspect, the method may further include the steps of:
  operating the valve to prevent the flow of pressurized fluid from flowing through the pressure control infusion tube and pressure control infusion needle;
  removing the pressure control infusion needle from the further incision; and
  allowing the further incision to self-seal.

In another aspect, the method may further include the step of:
  suturing the first incision while feeding pressurized fluid into the intraocular cavity through the pressure control infusion tube and pressure control infusion needle.

In yet another aspect, the method may further include the step of:
  removing the one or more surgical instruments from the one or more additional incisions while feeding pressurized fluid into the intraocular cavity through the pressure control infusion tube and pressure control infusion needle.

In another aspect, the method may further include the step of:
  suturing at least one of the one or more additional incisions while feeding pressurized fluid into the intraocular cavity through the pressure control infusion tube and pressure control infusion needle.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward an eye surgery device and method for providing and maintaining fluid (liquid and/or air) pressure within an eye during various surgical procedures.

Figure 1:
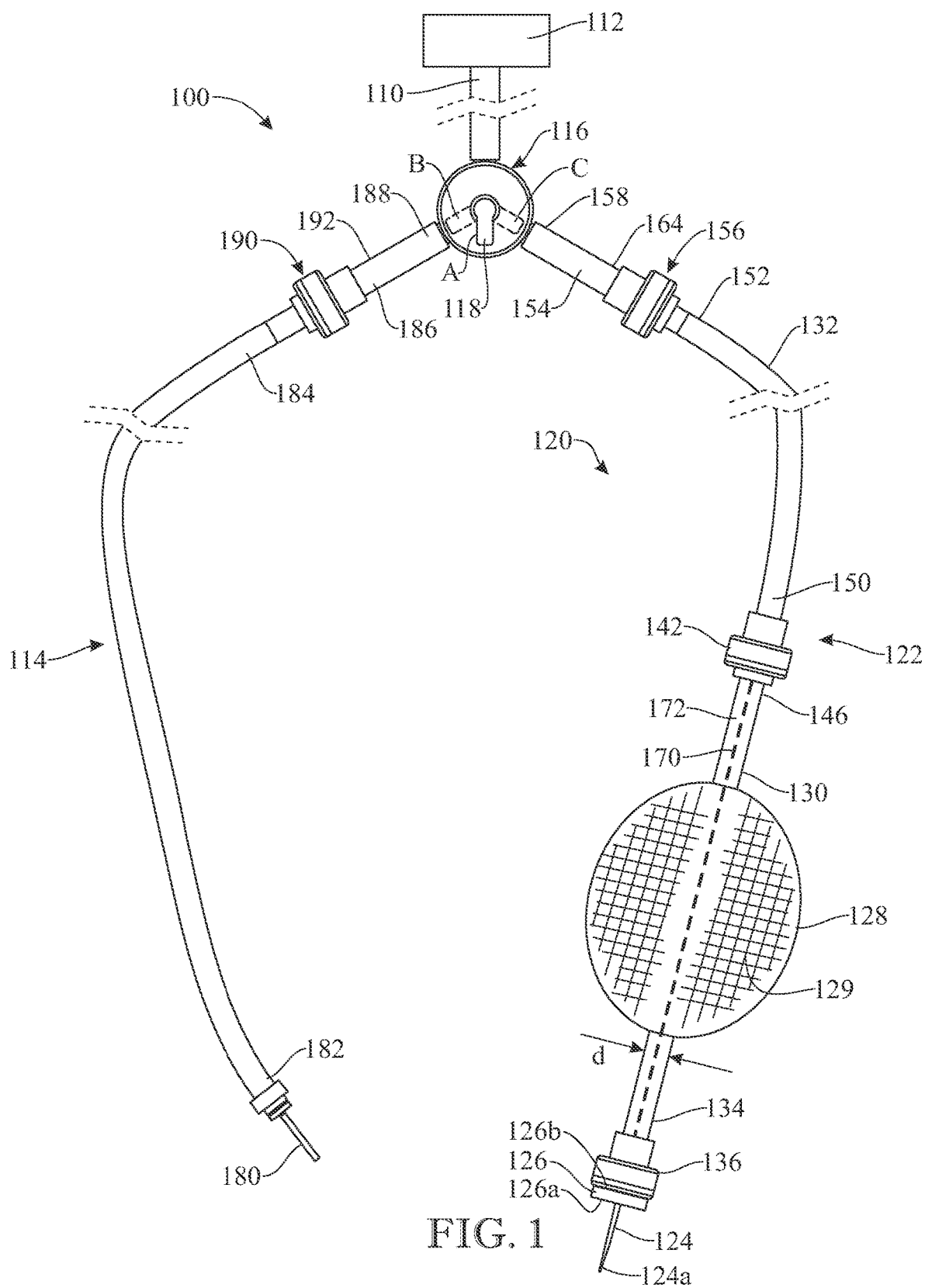
FIG. 1 presents an isometric view of a vitrectomy surgical device, including an eye chamber pressure maintainer, in accordance with a first illustrative embodiment of the present invention.
Figure 2:
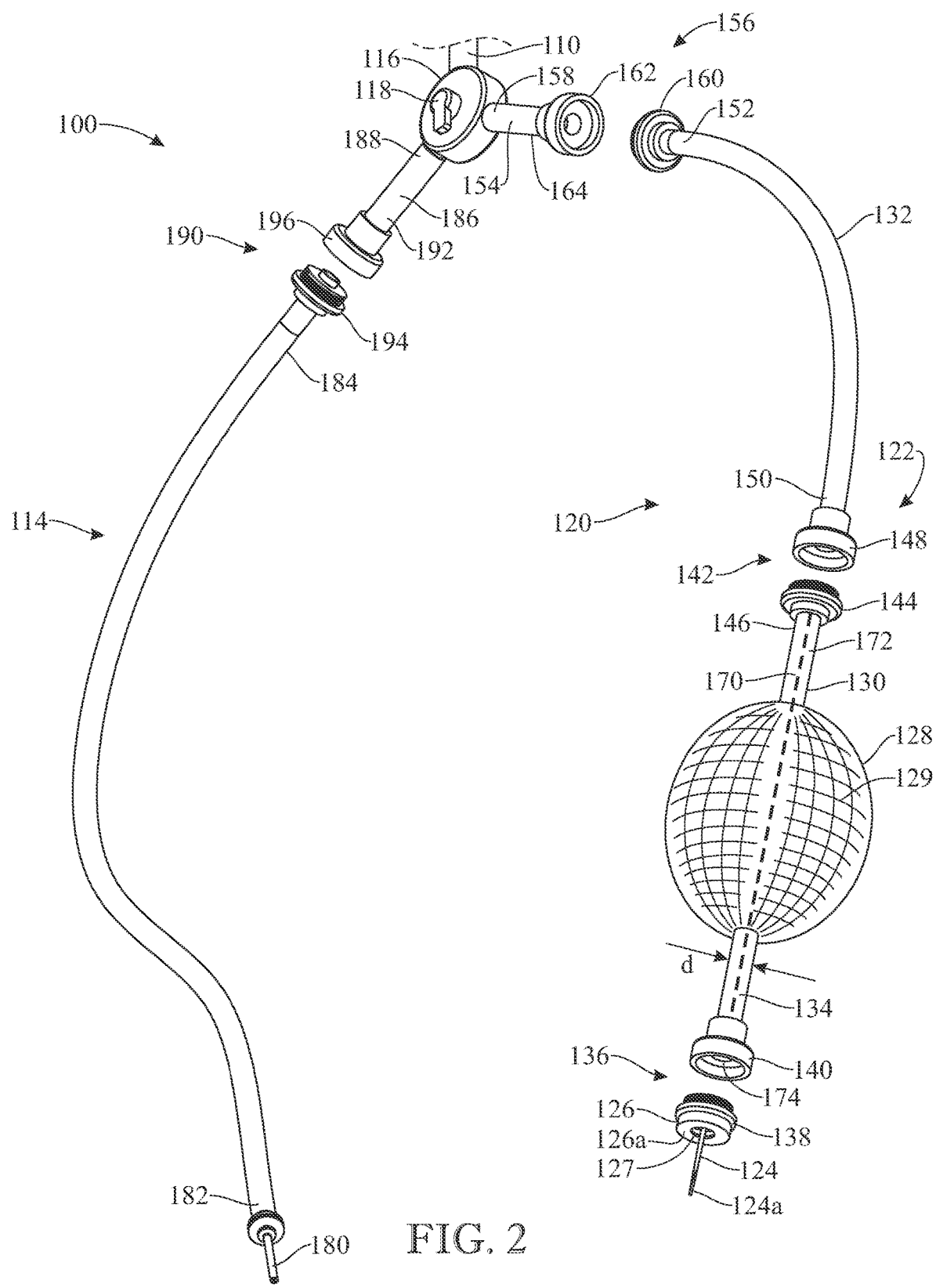
FIG. 2 presents an isometric view, with parts separated, of the vitrectomy surgical device illustrated in FIG. 1.

Referring to FIGS. 1-8, and initially with regard to FIGS. 1 and 2, an intraocular pressure control device for maintaining adequate posterior chamber pressure during eye surgery, hereinafter pressure control device 100, is illustrated in accordance with an exemplary embodiment of the present invention. As shown, the pressure control device 100 generally includes a fluid source tube 110 connected to a source of fluid pressure 112 (source of pressurized fluid) and a primary or main infusion tube 114 extending from the fluid source tube 110 for direct infusion of fluid pressure into an eye of a patient. The main infusion tube 114 is connected to the fluid source tube 110, and thus to the source of fluid pressure 112, through an externally-operable valve or stopcock 116, which controls the flow of fluid pressure emanating from the source of fluid pressure 112 to the main infusion tube 114. A switch or lever 118 provided on the stopcock 116 to allow an operator (e.g., a surgeon) to manually adjust the flow of fluid delivered by the stopcock 116 as will be described in detail hereinafter. The source of fluid pressure 112 can be portable or fixed and may include various tanks, pumps, etc.

The pressure control device 100 additionally includes a posterior chamber pressure maintainer or pressure maintainer 120 for maintaining adequate fluid pressure within the eye during removal of the main infusion tube 114 and any other surgical devices inserted into the eye for the purpose of surgery as discussed in more detail hereinbelow. The pressure maintainer 120 is also connected to the stopcock 116 and generally includes a pressure control infusion tube 122 terminating in a small diameter or small-gauge, hollow infusion needle 124. As will be described hereinafter, the needle 124 is configured to form a relatively small perforation to penetrate the eye, and to maintain a stable position, hand-free, once inserted into the eye, allowing the surgeon or user to address any leaking sclerotomy wounds while the pressure maintainer 120 remains in place to provide continued fluid pressure within the eye as discussed in more detail hereinbelow. The pressure maintainer 120 can present any applicable size, and is preferably long enough to connect from the eyes to the bridge of the nose of the patient. The pressure maintainer 120 may include extra length and/or sufficient flexibility to allow the surgeon or user to form one or more bends in the pressure control infusion tube 122 to encourage a perpendicular orientation of the infusion needle 124 into an eye wall.

The needle 124 can be sized so that it is small enough for the relatively small wound or puncture created by the needle 124 to self-seal but large enough to receive and transport proper fluid flow from the source of inflation fluid 112 or a pump associated therewith. For example, the needle 124 may be a 27, 30 or 32 gauge needle and have a length from ⅛ to ¼ of an inch, such as depending on the patient. It should be noted that the infusion needle 124 must be long enough that it safely and fully enters into the intravitreal space, but short enough that it does not risk contacting the intraocular tissues. The infusion needle 124 may have a beveled pointed edge 124a to minimize trauma to an eye wall as the infusion needle 124 is inserted there through.

As further shown in FIGS. 1 and 2, a stabilizing base 126 is affixed to the third tube 122 adjacent to the small-gauge infusion needle 124. The stabilizing base 126 is preferably rigid and is fixed (i.e. non movable) relative to the infusion needle 124 and is configured to stabilize the infusion needle 124 relative to the eye. More specifically, the stabilizing base 126 is configured to sit flush onto the eye wall while the needle 124 if fully inserted into the eye. For example, the stabilizing base 126 may be provided with a smooth distal surface or side 126a configured to rest against the eye. In some embodiments, as shown, the distal side 126a may be flat, to minimize friction against the eye while providing lateral stability to the needle. Having the stabilizing base 126 in place, flush to the eye wall, contributes to prevent torqueing of the needle 124. In some embodiments, the stabilizing base 126 may be formed as a small circular piece; however, alternative shapes are contemplated without departing from the scope of the present disclosure. The stabilizing base 126 may have a through opening 127, wherein the needle extends outwardly and distally from the opening 127 and the distal side 126a. For instance, the stabilizing base 126 may be annular in shape and the through opening 127 may be arranged at or near a center of the stabilizing plate 126. In some non-limiting examples, the stabilizing base 126 may be approximately 2 to 4 mm in width or diameter. Alternatively or additionally, the stabilizing base 126 may be approximately 2 to 4 mm thick. In some embodiments, the stabilizing base 126 may be formed as a plate, with the aforementioned distal side 126a and a proximal side 126b of the stabilizing base 126 arranged generally parallel to one another.

An enlarged member or grip 128 is provided on the pressure control infusion tube 122 to facilitate grasping the relatively thin, pressure control infusion tube 122 with the user's finger tips. The grip 128 is preferably fixed along the length of the pressure control infusion tube 122 and is preferably wider or larger than a diameter "d" of the pressure control infusion tube 122. As shown, the grip 128 is arranged at or near the stabilizing plate 126, such as at a distance of up to 2 inches, and more preferably, between 1 and 2 inches, from the stabilizing plate 126. The grip 128 assists the user in maneuvering the infusion tube 122, and more specifically, in inserting the infusion needle 124 into the eye and in manipulating the pressure control infusion tube 122 relative to the eye. The grip 128 may be made from one or more lightweight materials, such as plastic, wherein said lightweight material(s) may contribute to the ability of the infusion needle 124 to maintain the position established by the surgeon or user as described hereinbelow. Ira some embodiments, the grip 128 may be provided with a non-slip or increased-friction outer surface (indicated by reference numeral 129) to enhance the grip of the surgeon's hand thereon. Non-limiting examples of said increased-friction outer surface include a non-slip material (e.g., rubber), a rough texture, bumps or ridges, recesses, engravings, or combinations thereof.

The pressure control device 100 may be provided as a single or integral unit with the infusion tubes 110, 114 and 120, respectively, preassembled to the stopcock 116 or may be provided as a modular unit allowing the surgeon or user to assemble the pressure control device 100 at the operative site as it is being used. For example, the pressure control infusion tube 120 may include a distal infusion tube 130 and a proximal or extension infusion tube 132 connected to the distal infusion tube 130 and extending from the stopcock 116. In cases where the pressure control device 100 is provided as a modular unit, the pressure control device 100 allows the surgeon or user to only connect the pressure maintainer 120 when or as needed.

The infusion needle 124 may be connected to the pressure control infusion tube 122 in a variety of ways either non-removably (e.g., directly) or removably. In this particular embodiment, the infusion needle 124 and the stabilizing base 126 are connected to a first or distal end 134 of the distal infusion tube 130 by a first connector 136. The first connector 136, and in general any or all the connectors described herein, may be a "luer-lock" type connector. The first connector 136 may have a male end 138 affixed to the infusion needle 124 and stabilizing base 126 and a female end 140 connected to the distal end 134 of the distal infusion tube 130, wherein the male and female ends 138 and 140 are configured to interlock with one another in a preferably disconnectable manner.

Similarly, the proximal infusion tube 132 extends from and is removably connected to the distal infusion tube 130 by a second connector 142. The second connector 142 may include a male end 144 affixed to a second or proximal end 146 of the distal infusion tube 130 and a female end 148 affixed to a first or distal end 150 of the proximal infusion tube 132, wherein the male and female ends 144 and 148 are configured to interlock with one another in a preferably disconnectable manner.

As noted hereinabove, the proximal infusion tube 132 extends from the stopcock 116 and may be non-removably connected (e.g., directly connected) thereto or, in other embodiments such as this particular embodiment, be removably attached thereto to further allow a user to assembly the pressure maintainer 120 to the stopcock 116 as desired. For example, in the disclosed embodiment, the pressure control device 100 further includes an extension tube 154 extending from the stopcock 116 and removably attached to a proximal end of the proximal infusion tube 132 of the pressure maintainer 120 by a third connector 156. The extension tube 154 includes a proximal end 158 extending from the stopcock 116, and a distal end 164. The third connector 156 may include a male end 160 affixed to a proximal end 152 of the proximal infusion tube 132 and a female end 162 affixed to the distal end 164 of the extension tube 154, wherein the male and female ends 160 and 162 are configured to interlock with one another in a preferably disconnectable manner.

It should be noted that the pressure control infusion tube 122, including the distal infusion tube 130 and the proximal infusion tube 132, is hollow such that the hollow infusion needle 124 is in fluid communication with the source of fluid pressure 112 through the fluid source tube 110, the stopcock 116 and the extension tube 154, when the stopcock 116 is operated to enable such fluid communication.

Additionally, it should be further noted that all tubes described herein are preferably flexible, and that the pressure control infusion tube 122 is more preferably plastically flexible, such that a user may bend or flex the pressure control infusion tube 122 and the pressure control infusion tube 122 may retain said deformed shape. For instance, in some embodiments, tubular walls of the pressure control infusion tube 122 may be formed of a plastically-flexible material. In other embodiments, the pressure control infusion tube 122 may include a plastically-deformable material or element, such as, but not limited to, a plastically-flexible wire 170. For example, the flexible wire 170 may be affixed to or embedded in the pressure control infusion tube 122 and permit the user to manipulate and contribute to maintain the position and orientation of the pressure control infusion tube 122 and the infusion needle 124 relative to the surface of the eye. In the present embodiment, the flexible wire 170 is provided on an outer surface 172, or embedded in a wall 174, of the distal infusion tube 130 of the pressure control infusion tube 122. As shown, in this particular embodiment, the grip 128 is also affixed to the distal infusion tube 130 and extends outwardly from the outer surface 172 of the distal infusion tube 130. Having both the grip 128 and the flexible wire 170 located along a distal section of the pressure control infusion tube 122 (e.g., along the distal infusion tube 130) permits the user to manipulate both the infusion needle 124 and the section of the pressure control infusion tube 122 by moving the grip 128; for example, the user may reorient the infusion needle 124 by use of the grip 128 until the infusion needle 124 is properly inserted and perpendicularly arranged relative to the eye and stabilized by the stabilizing base 126, and then may bend or manipulate the shape of the distal infusion tube 130 by carefully continuing to operate the grip 128 such that the distal infusion tube 130 is manipulated and deformed to the desired shape and the flexible wire 170 maintains the manipulated shape of the distal infusion tube 130, while the stabilizing base 126 maintains the infusion needle 124 properly oriented.

As noted hereinabove, the main infusion tube 114 is connected to the fluid source tube 110, and thus the source of infusion fluid 112, through the stopcock 116 and provides the primary source of infusion fluid to the eye during a surgical procedure. The main infusion tube 114 includes a relatively large gauge infusion end or needle 180 provided on a distal end 182 of the main infusion tube 114 (relatively large gauge being understood as the needle 180 having a larger diameter than the infusion needle 124).

As with the pressure maintainer 120, the main infusion tube 114 may be non-removably (e.g., directly) or removably attached to the stopcock 116. For example, a proximal end 184 of the main infusion tube 114 may be removably attached to a further extension tube 186, which includes a proximal end 188 affixed to the stopcock 116 and extends from the stopcock 116. A fourth connector 190 may disconnectably connect a distal end 192 of the extension tube 186 to the proximal end 184 of the main infusion tube 114. A male end 194 of the fourth connector 190 may be affixed to the proximal end 184 of the main infusion tube 114 and a female connector of the fourth connector 190 may be affixed to the distal end 192 of the extension tube 186. While not specifically shown, the main infusion tube 114 and the extension tube 186 are also hollow such that the large gauge needle 180 is in fluid communication with the source of fluid pressure 112 through the fluid source tube 110 and the stopcock 116.

The stopcock 116 is operable, through manipulation of the lever 118 on the stopcock 116, to selectively direct fluid pressure from the source of fluid pressure 112 to the main infusion tube 114, or to the pressure control infusion tube 122 and the pressure maintainer 120. For instance, as shown in FIG. 1, in some embodiments, such as the present embodiment, the stopcock 116 may be configured to adopt: a first or closed position "A", in which the stopcock 116 prevents fluid communication between the fluid source tube 110 and both of the extension tubes 186 and 154; a second position "B", in which the stopcock 116 prevents fluid communication between the fluid source tube 110 and the extension tube 154, and provides fluid communication between the fluid source tube 110 and the extension tube 186; and a third position "C", in which the stopcock 116 provides fluid communication between the fluid source tube 110 and the extension tube 154, and prevents fluid communication between the fluid source tube 110 and the extension tube 186.

Figure 3:
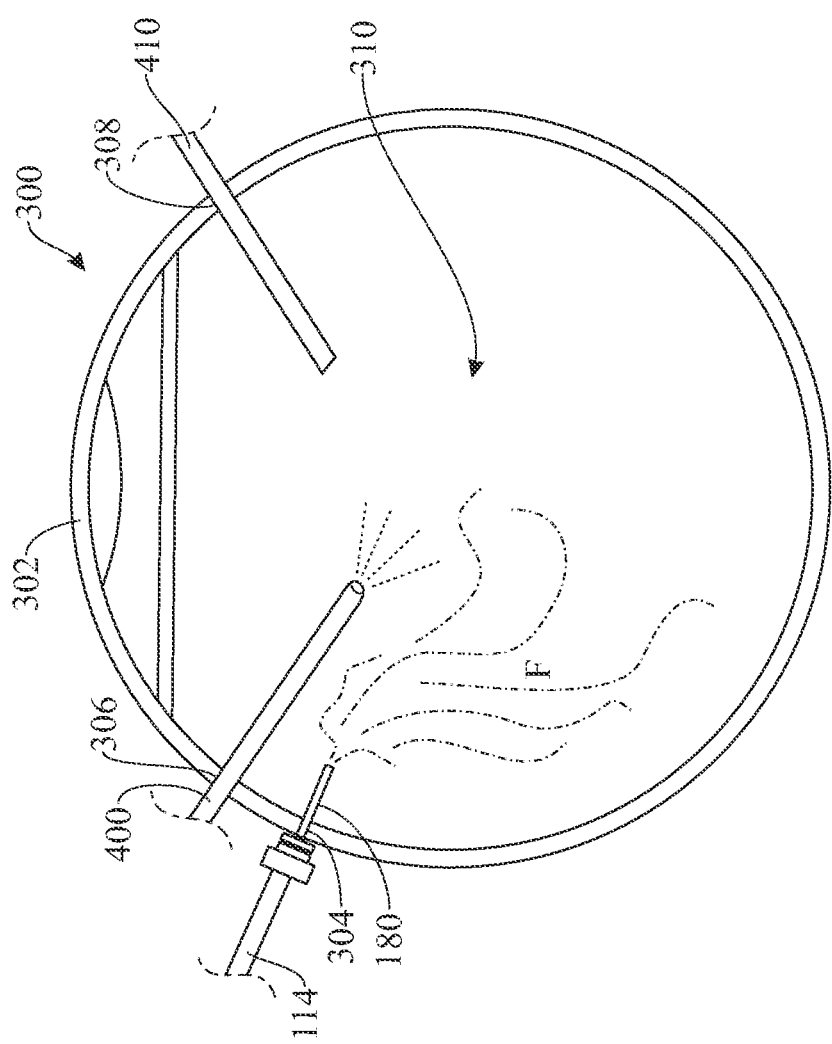
FIG. 3 presents a side plan view of an eye during the initial stages of performing a vitrectomy after performing a three port insertion of a primary infusion cannula, an optical cannula and an access cannula for the insertion of surgical instruments into an interior of the eye and initiation of infusion into the interior of the eye.

Turning now to FIGS. 3-8, an advantageous method of use of the pressure control device 100 of FIGS. 1 and 2 to perform an eye surgery procedure in accordance with an embodiment of the invention will now be described. Referring initially to FIG. 3, in a first step 200 (FIG. 8) a three-port vitrectomy procedure is performed by inserting one or more cannula ports (not shown) into an eye 300 of patient through a wall 302 of the eye 300. This creates three relatively large incisions 304, 306 and 308 in the eye wall 302 to accommodate the ports. In order to maintain pressure within the eye 300, the main infusion tube 114 including the large gauge needle 180 is inserted through the first incision 304, or a cannula port, pre-positioned through the first incision 304, and the lever 118 of the stop cock 116 is moved from the closed position "A" (FIG. 1) preventing the flow of fluid pressure out of the stopcock 116 to the second position "B" to initially direct the flow of fluid pressure "F" from the source of fluid pressure 112 to the main infusion tube 114 and thus to the infusion needle 180 and into an intraocular cavity 310 of the eye 300.

Thereafter, a diagnostic device 400, for example a light source, laser source, camera, etc., is inserted through the second incision 306, or a cannula port pre-positioned through the second incision 306. The surgeon can then insert an operative surgical device 410 such as, but not limited to, a mechanical or laser cutter, ablater, or other operative device, through the third incision 308, or a cannula port pre-positioned through the third incision 308, to perform the surgical procedure.

During the course of the three-port vitrectomy, if the surgeon anticipates that there might be wound leaks occurring at one of the three incisions 304, 306 or 308 during the surgery or upon removal of the large gauge infusion needle 180, the diagnostic device 400 or the operative surgical device 410, from the respective incisions 304, 306 and 308, or the surgeon wants or needs the added protection of the pressure maintainer 120 to assist in maintaining adequate fluid pressure "F" within the eye 300, the pressure maintainer may be connected to the source of fluid pressure 112 by assembling the pressure maintainer 120 to the source of fluid pressure 112 through the second and third connectors 142 and 156, respectively and the stopcock 116 (FIGS. 1 and 2) in a second step 202 and a third step 204 (FIG. 8), if not previously assembled. The infusion needle 124 and the stabilizing base 126 are attached to the distal infusion tube 130 through the first connector 136 in advance of, or after, connecting the pressure maintainer 120 to the source of fluid 112.

Figure 4:
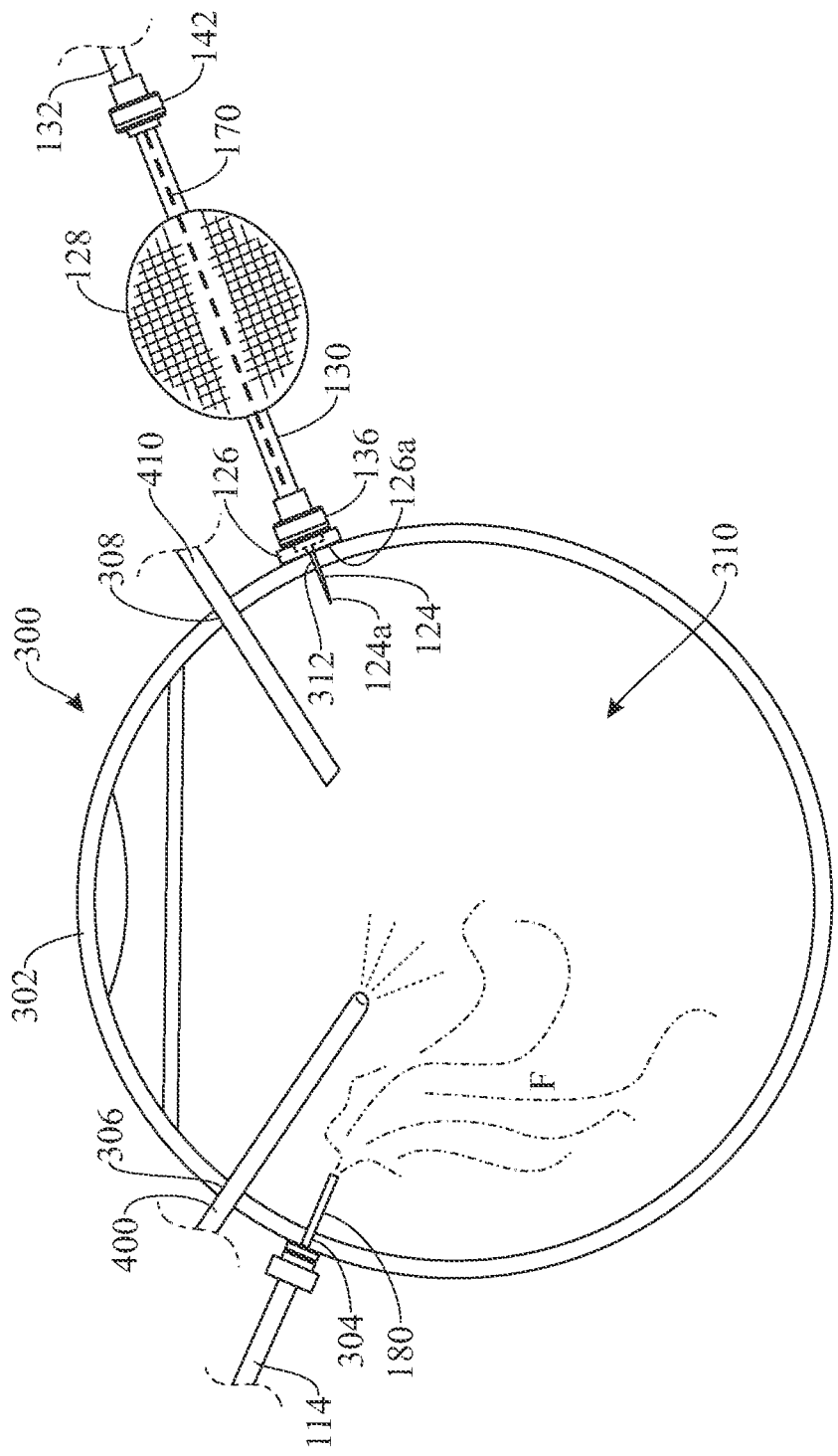
FIG. 4 presents a side plan view of the eye similar to FIG. 3 and illustrating the insertion of the chamber pressure maintainer into the eye.

Referring now to FIG. 4, as noted above the pressure maintainer 120 may be positioned in the eye 300 before, during or after the vitrectomy or surgical procedure to assist in maintaining adequate fluid pressure "F" within the eye 300. For example, in a fourth step 206, the user may hold the grip 128 of the pressure maintainer 120 and manipulate the pressure maintainer 120 such that, in a fifth step 208, the user inserts the small gauge, infusion needle 124 through the pars plana or eye wall 302 until the stabilizing base 126 is flush with the eye wall 302. The insertion of the infusion needle 124 through the eye wall 302 creates a minimal or relatively small puncture or incision 312 through the eye wall 302 which can easily self-seal without the danger of leaking. The surgeon may also further stabilize the distal end 134 of the distal infusion tube 130 and the infusion needle 124 of the pressure maintainer 120 by taping the stabilizing base 126 to a drape or other temporary covering provided over the eye 300.

Figure 5:
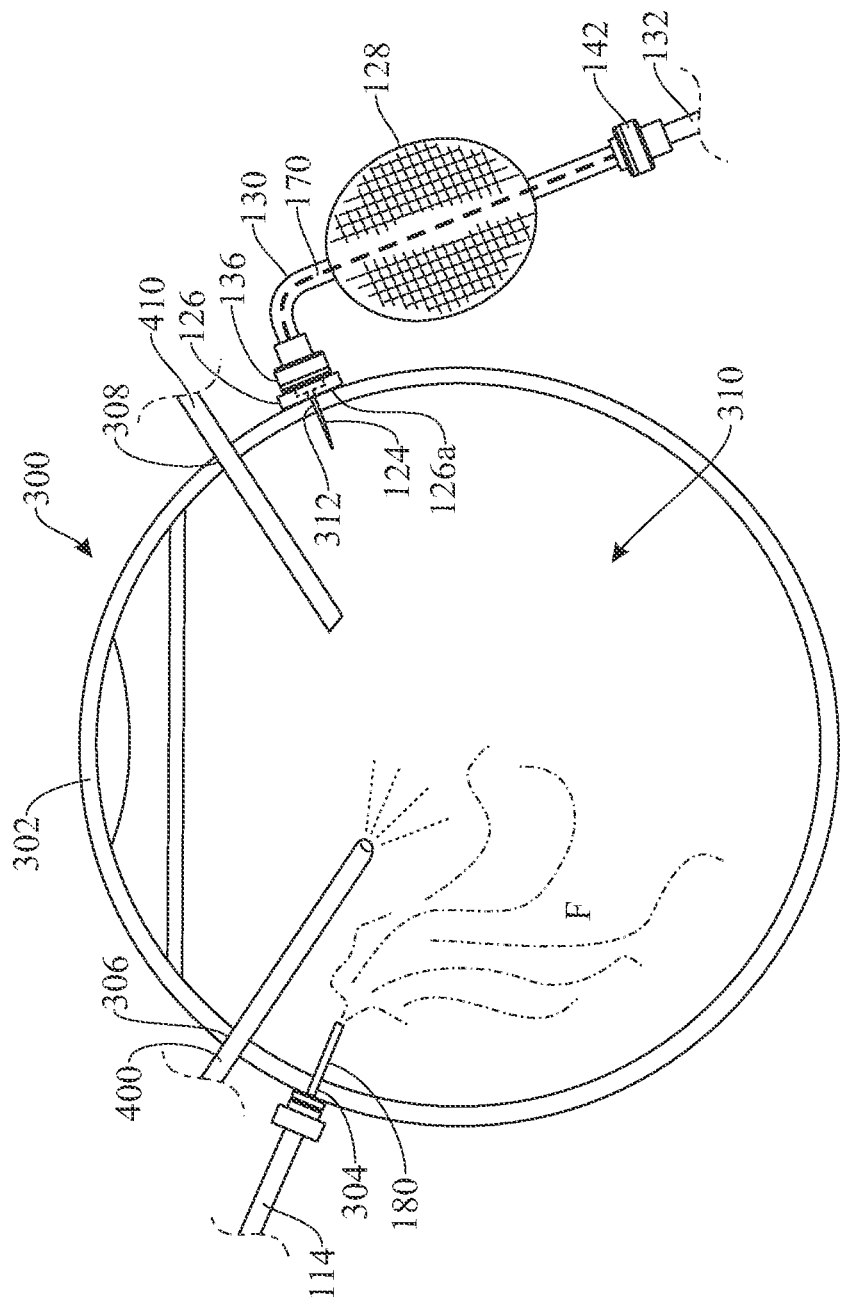
FIG. 5 presents a side plan view similar to FIG. 4 with a pressure line of the chamber pressure being manipulated to maintain a needle of the chamber pressure maintainer perpendicular to a wall of the eye.

In a sixth step 210 as shown in FIGS. 4 and 5, the surgeon may then manipulate the distal infusion tube 130 by bending the distal infusion tube 130 to a desired position or orientation relative to the eye wall 302. The bent or deformed flexible wire 170 remains in the bent or deformed position established by the surgeon, and thereby maintains the distal infusion tube 130 in the bent condition without the surgeon having to hold the grip 128. Thus, the self-stabilized (or hands-free-stabilized) pressure maintainer 120 allows both hands of the surgeon to remain available to complete other steps of the surgery.

Figure 6:
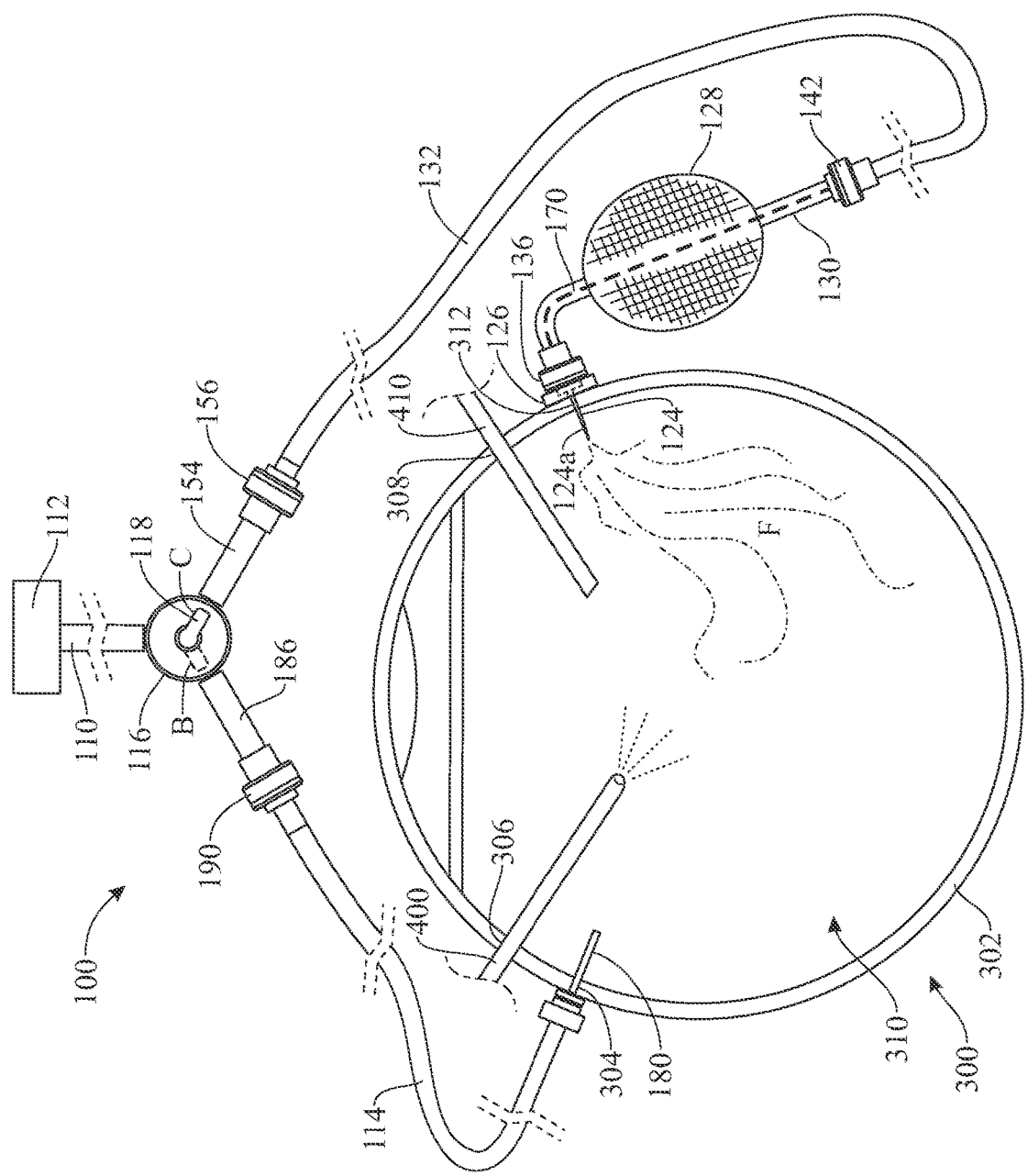
FIG. 6 presents a side plan view similar to FIG. 5 illustrating the cessation of infusion through the primary infusion cannula and initiation of infusion into the eye through the chamber pressure maintainer.
Figure 8:
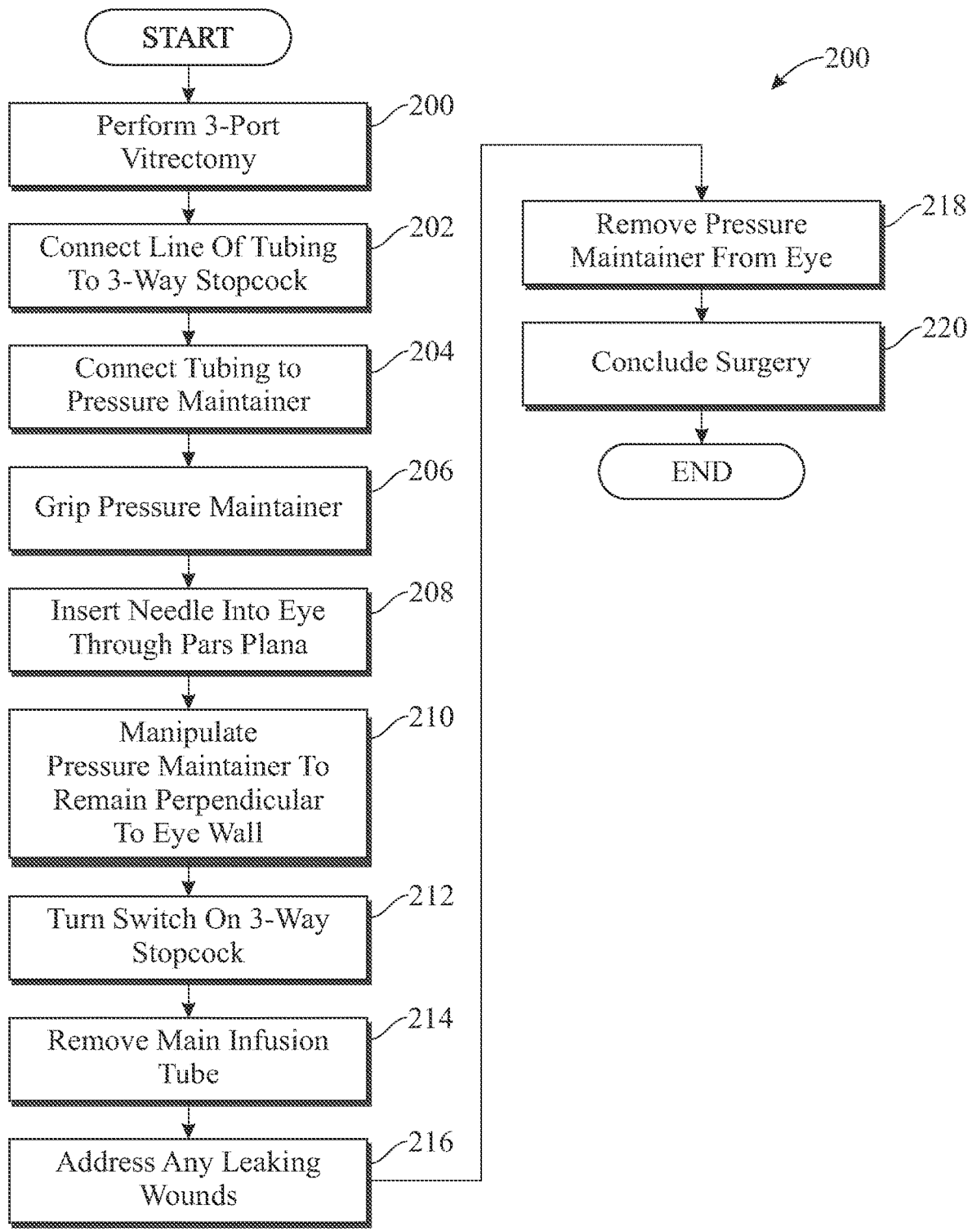
FIG. 8 presents a flow chart for a method of performing a vitrectomy utilizing the chamber pressure maintainer of the present invention.

Referring to FIG. 6, once the pressure maintainer 120 has been properly positioned against and into the eye 300, the lever 118 of the stopcock 116 may be moved from position "B" to position "C" switching or diverting the flow of fluid pressure from the source of fluid pressure 112 from the main infusion tube 114 and directing the flow of fluid pressure "F" into the pressure maintainer 120 in a seventh step 212 (FIG. 8). The pressure maintainer 120, through the infusion needle 124, provides fluid pressure into, and helps maintain the fluid pressure "F" within, the intraocular cavity 310 of the eye 300, such as in the event of fluid leaking through the incision 306 prior to or after removing the needle 180 from the eye 300.

Figure 7:
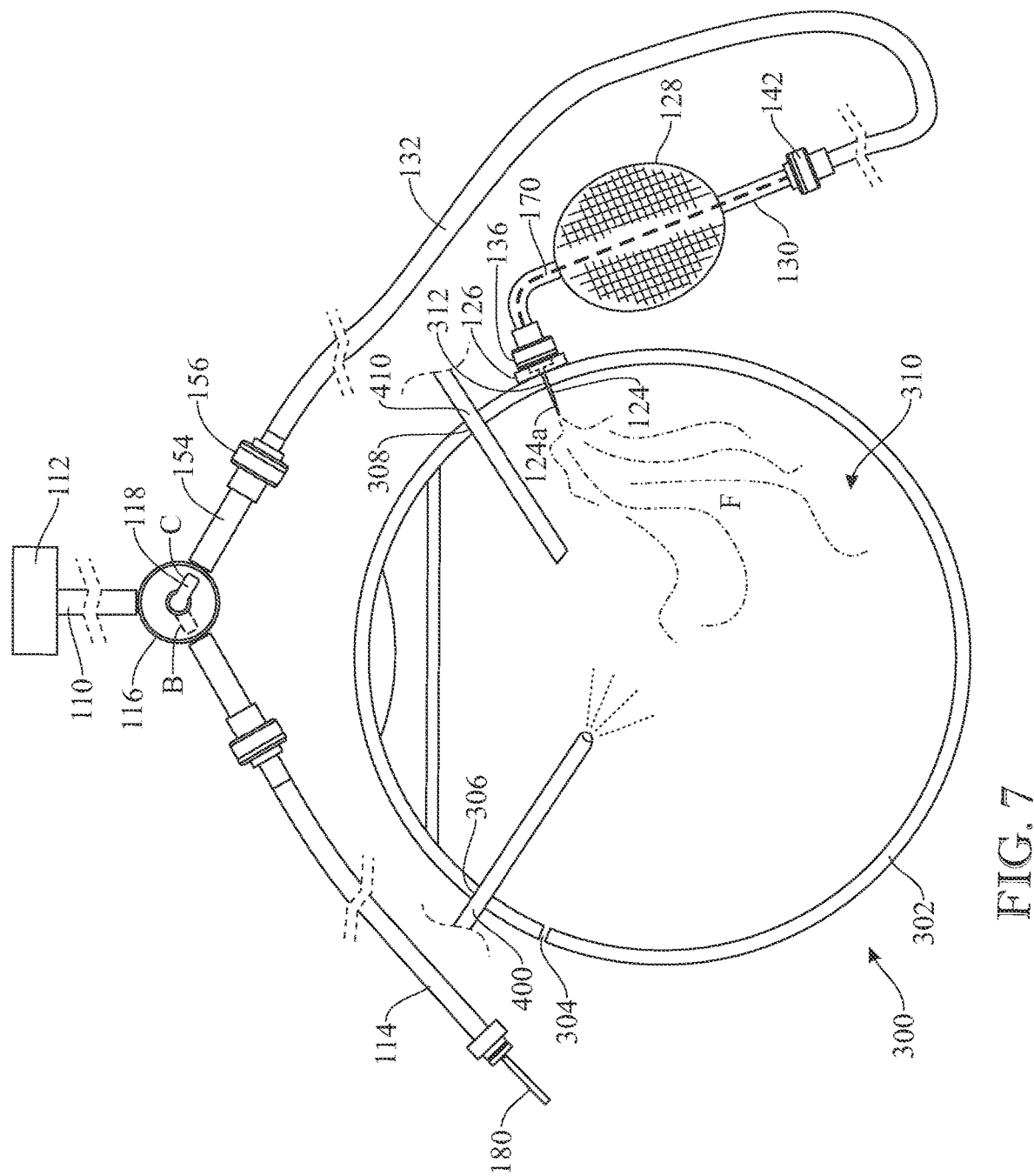
FIG. 7 presents a side plan view of the eye during removal of the primary intlision cannula and maintenance of the fluid pressure within the eye chamber through the disclosed chamber pressure maintainer.

For example, referring to FIG. 7 and eighth step 214 of FIG. 8, with the infusion needle 124 in place and providing adequate fluid pressure to the intraocular cavity 310, the main infusion tube 114 may be safely removed once the surgical procedure has been completed. More specifically, the large gauge infusion needle 180 may be removed through the first incision 304 while adequate eye pressure is maintained through the pressure control infusion tube 122 of the pressure maintainer 120. While not specifically shown, the diagnostic device 400 and the operative surgical device 410 may also be removed through their respective second and third incisions 306 and 308 in the eye wall 302. The first, second and third incisions 304, 306 and 308 may then be allowed to self-seal, or may alternatively require suturing or other surgical assistance to remain closed during the healing process in a ninth step 216 (FIG. 8).

Once the surgeon is satisfied that all cannula/incision wounds have been satisfactorily closed, the surgeon moves the lever 118 of the stopcock 116 back to closed position "A" shutting off the flow of fluid pressure to the pressure maintainer 120. Thereafter, the stabilizing base 126 is unsecured from the drape or eye 300 (if previously secured) and the infusion needle 124 is pulled out of the eye 300 in a tenth step 218 (FIG. 8) thus concluding the surgery in an eleventh step 220 (FIG. 8). Due to the relatively small incision or puncture created by the small gauge infusion needle 124 through the eye wall 302, there is minimal or no risk of that small incision 312 not properly and safely self-sealing.

Thus, the disclosed intraocular pressure control device 100, and in particular the pressure maintainer 120, provide a solution to the problem of dangerous loss of eye pressure during and at the end of eye surgery upon removal of the an infusion cannula or main infusion tube 114 and other cannula used during surgery.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A pressure control device for maintaining fluid pressure within an intraocular cavity during eye surgery, the pressure control device comprising:
  a valve, configured to connect to a source of pressurized fluid;
  a pressure maintainer, comprising:
    a plastically flexible, pressure control infusion tube having a distal end and a proximal end, wherein the proximal end of the pressure control infusion tube is connectable to the valve,
    a stabilizing base provided at the distal end of the pressure control infusion tube and extending radially outward of the pressure control infusion tube,
    a pressure control infusion needle extending distally from the stabilizing base and the distal end of the pressure control infusion tube, wherein the pressure control infusion needle is in fluid communication with the pressure control infusion tube, and
    a grip carried by the pressure control infusion tube distally to the stabilizing base, and at or near the stabilizing base, the grip having a width larger than a diameter of the pressure control infusion tube; and
  a main infusion tube, comprising a proximal end and a distal end, wherein the proximal end of the main infusion tube is connectable to the valve, and wherein the distal end of the main infusion tube carries a main infusion needle having a greater gauge than the pressure control infusion needle; wherein
  the valve is operable to switch between:
    a first position, in which the valve provides fluid communication from the source of pressurized fluid to the main infusion tube and prevents fluid communication from the source of pressurized fluid to the pressure control infusion tube, and
    a second position, in which the valve prevents fluid communication from the source of pressurized fluid to the main infusion tube and provides fluid communication from the source of pressurized fluid to the pressure control infusion tube.

2. The pressure control device of claim 1, further comprising a connector attached to the proximal end of the pressure control infusion tube, the connector configured to provide a disconnectable connection between the proximal end of the pressure control infusion tube and a source of pressurized fluid.

3. The pressure control device of claim 2, wherein the connector is a luer-lock connector.

4. The pressure control device of claim 1, wherein the pressure control infusion tube comprises a distal infusion tube and a proximal infusion tube connected to one another by a disconnectable connection connecting a distal end of the proximal infusion tube to a proximal end of the distal infusion tube, wherein a proximal end of the proximal infusion tube provides the proximal end of the pressure control infusion tube, and a distal end of the distal infusion tube provides the distal end of the pressure control infusion tube, and further wherein the pressure control infusion needle and the stabilizing base are located at the distal infusion tube.

5. The pressure control device of claim 4, wherein the disconnectable connection is a luer-lock connection.

6. The pressure control device of claim 1, wherein the pressure control infusion needle is attached to the distal end of the pressure control infusion tube by a disconnectable connection.

7. The pressure control device of claim 6, wherein the disconnectable connection is a luer-lock connection.

8. The pressure control device of claim 1, wherein the pressure control infusion needle has a gauge from 27 to 32.

9. The pressure control device of claim 1, wherein a distal surface of the stabilizing base facing the pressure control infusion needle is flat.

10. The pressure control device of claim 1, wherein the stabilizing base comprises a central opening from which the pressure control infusion needle extends outwardly and distally.

11. The pressure control device of claim 1, wherein the valve is further operable to switch to a third position, in which the valve prevents fluid communication from the source of pressurized fluid to the main infusion tube and prevents fluid communication from the source of pressurized fluid to the pressure control infusion tube.

12. The pressure control device of claim 1, wherein the main infusion tube is connectable to the valve by a disconnectable connection.

13. The pressure control device of claim 1, wherein the disconnectable connection is a luer-lock connection.

14. A pressure control device for maintaining fluid pressure within an intraocular cavity during eye surgery, the pressure control device comprising:
 a valve;
 a pressure maintainer, comprising:
  a plastically flexible, pressure control infusion tube having a distal end and a proximal end, wherein the proximal end of the pressure control infusion tube is connectable to the valve,
  a stabilizing base provided at the distal end of the pressure control infusion tube and extending radially outward of the pressure control infusion tube,
  a pressure control infusion needle extending distally from the stabilizing base and the distal end of the pressure control infusion tube, wherein the pressure control infusion needle is in fluid communication with the pressure control infusion tube, and
  a grip carried by the pressure control infusion tube distally to the stabilizing base, and at or near the stabilizing base, the grip having a width larger than a diameter of the pressure control infusion tube; and
 a main infusion tube, comprising a proximal end and a distal end, wherein the proximal end of the main infusion tube is connectable to the valve, and wherein the distal end of the main infusion tube carries a main infusion needle having a greater gauge than the pressure control infusion needle; wherein
 the valve is operable to switch between:
  a first position, in which the valve provides fluid communication from the source of pressurized fluid to the main infusion tube and prevents fluid communication from the source of pressurized fluid to the pressure control infusion tube,
  a second position, in which the valve prevents fluid communication from the source of pressurized fluid to the main infusion tube and provides fluid communication from the source of pressurized fluid to the pressure control infusion tube, and
  a third position, in which the valve prevents fluid communication from the source of pressurized fluid to the main infusion tube and prevents fluid communication from the source of pressurized fluid to the pressure control infusion tube.

15. A method of performing an eye surgery procedure while maintaining fluid pressure within an intraocular cavity, comprising:
 providing a pressure control device comprising:
  a valve,
  a pressure maintainer, comprising:
   a plastically flexible, pressure control infusion tube having a distal end and a proximal end, the proximal end connected to the valve,
   a stabilizing base provided at the distal end of the pressure control infusion tube and extending radially outward of the pressure control infusion tube,
   a pressure control infusion needle extending distally from the stabilizing base and the distal end of the pressure control infusion tube, wherein the pressure control infusion needle is in fluid communication with the pressure control infusion tube, and
   a grip carried by the pressure control infusion tube distally to the stabilizing base, and at or near the stabilizing base, the grip having a width larger than a diameter of the pressure control infusion tube, and
  a main infusion tube, comprising a proximal end and a distal end, wherein the proximal end of the main infusion tube is connected to the valve, and wherein the distal end of the main infusion tube carries a main infusion needle having a greater gauge than the pressure control infusion needle;
 connecting the valve to a source of pressurized fluid;
 inserting the main infusion needle through an eye wall and into an intraocular cavity of an eye through a first incision in the eye wall;
 operating said valve to direct a flow of pressurized fluid from the source of pressurized fluid through the main infusion tube and main infusion needle and into the intraocular cavity;
 inserting one or more surgical instruments into the intraocular cavity through one or more additional incisions in the eye wall;
 performing a surgical procedure with the one or more surgical instruments;
 forming a further incision through the eye wall by inserting the pressure control infusion needle through the eye wall, the further incision being smaller than the first incision;
 operating the valve to direct the flow of pressurized fluid through the pressure control infusion tube and pressure control infusion needle and into the intraocular cavity; and
 removing the main infusion needle from the first incision while feeding pressurized fluid into the intraocular cavity through the pressure control infusion tube and pressure control infusion needle.

16. The method of claim 15, further comprising the steps of:
 operating the valve to prevent the flow of pressurized fluid from flowing through the pressure control infusion tube and pressure control infusion needle;
 removing the pressure control infusion needle from the further incision; and
 allowing the further incision to self-seal.

17. The method of claim 15, further comprising the step of:
 suturing the first incision while feeding pressurized fluid into the intraocular cavity through the pressure control infusion tube and pressure control infusion needle.

18. The method of claim 15, further comprising the step of:
 removing the one or more surgical instruments from the one or more additional incisions while feeding pressurized fluid into the intraocular cavity through the pressure control infusion tube and pressure control infusion needle.

19. The method of claim 18, further comprising the step of:
   suturing at least one of the one or more additional incisions while feeding pressurized fluid into the intraocular cavity through the pressure control infusion tube and pressure control infusion needle.

\* \* \* \* \*